(12) United States Patent
Coates et al.

(10) Patent No.: US 7,556,607 B2
(45) Date of Patent: Jul. 7, 2009

(54) DEVICES AND TECHNIQUES RELATING TO RANGE OF MOTION OF THE CERVICAL SPINE

(75) Inventors: Bradley J. Coates, Rossville, TN (US); Greg Marik, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 745 days.

(21) Appl. No.: 11/118,577

(22) Filed: Apr. 29, 2005

(65) Prior Publication Data

US 2006/0247557 A1 Nov. 2, 2006

(51) Int. Cl.
*A61F 5/00* (2006.01)
(52) U.S. Cl. .......................... 602/18; 602/19
(58) Field of Classification Search .............. 602/17–19; 600/424; 5/649–650
See application file for complete search history.

(56) References Cited

U.S. PATENT DOCUMENTS

| | | | |
|---|---|---|---|
| 4,494,261 A * | 1/1985 | Morrow ........................ | 5/636 |
| 4,586,515 A | 5/1986 | Berger | |
| 4,616,814 A | 10/1986 | Harwood-Nash et al. | |
| 4,821,355 A | 4/1989 | Burkhardt | |
| 4,893,808 A | 1/1990 | McIntyre et al. | |
| 5,002,269 A | 3/1991 | Jones | |
| 5,016,303 A | 5/1991 | Tanaka et al. | |
| 5,090,042 A | 2/1992 | Bejjani et al. | |
| 5,092,585 A | 3/1992 | Jones | |
| 5,099,859 A | 3/1992 | Bell | |
| 5,147,287 A | 9/1992 | Jewell et al. | |
| 5,203,346 A | 4/1993 | Fuhr et al. | |
| 5,305,750 A | 4/1994 | Makita | |
| 5,351,408 A | 10/1994 | Street | |
| 5,410,769 A | 5/1995 | Waterman | |
| 5,582,189 A | 12/1996 | Pannozzo | |
| 5,640,958 A | 6/1997 | Bonutti | |
| 5,709,649 A | 1/1998 | Chitwood | |
| 5,743,271 A | 4/1998 | Royo-Salvador | |
| 5,772,595 A | 6/1998 | Wotruba et al. | |
| 5,880,976 A | 3/1999 | DiGioia, III et al. | |
| 6,003,174 A | 12/1999 | Kantrowitz et al. | |
| 6,138,302 A | 10/2000 | Sashin et al. | |
| 6,143,003 A | 11/2000 | Cosman | |
| 6,151,733 A | 11/2000 | Takashima | |
| 6,205,411 B1 | 3/2001 | DiGioia, III et al. | |

(Continued)

FOREIGN PATENT DOCUMENTS

CA 2269173 10/2000

(Continued)

*Primary Examiner*—Michael A. Brown
(74) *Attorney, Agent, or Firm*—Krieg Devault (57) ABSTRACT

One embodiment of the present application is directed to: shaping a neck support to conform to a neck of a patient while the neck is configured with a desired lordosis of a cervical spine of the patient, performing a surgical procedure on the cervical spine of the patient based on the desired lordosis, and during or after the surgical procedure, holding the neck of the patient in the neck support to configure the neck with this desired lordosis, and pivoting the neck cradle about two or more different pivot axes as the neck is held to evaluate two or more different ranges of motion of the cervical spine of the patient.

25 Claims, 5 Drawing Sheets

U.S. PATENT DOCUMENTS

| | | |
|---|---|---|
| 6,442,777 B1 | 9/2002 | Pauli |
| 6,500,136 B2 | 12/2002 | Meyer |
| 6,514,219 B1 | 2/2003 | Guimond et al. |
| 6,557,195 B2 | 5/2003 | Dinkler |
| 6,565,577 B2 | 5/2003 | Cosman |
| 6,637,058 B1 | 10/2003 | Lamb |
| 6,671,537 B1 | 12/2003 | Bonutti |
| 6,684,095 B1 | 1/2004 | Bonutti |
| 6,697,659 B1 | 2/2004 | Bonutti |
| 2001/0047143 A1 | 11/2001 | Meyer |
| 2002/0050007 A1 | 5/2002 | Kim |
| 2003/0158015 A1 | 8/2003 | Watson |
| 2005/0245817 A1* | 11/2005 | Clayton et al. .............. 600/424 |

FOREIGN PATENT DOCUMENTS

| | | |
|---|---|---|
| WO | WO 98/17177 | 4/1998 |
| WO | WO 02/089923 A1 | 11/2002 |

* cited by examiner

DEVICES AND TECHNIQUES RELATING TO RANGE OF MOTION OF THE CERVICAL SPINE

BACKGROUND

The present invention relates to medical treatment of the spine, and more particularly, but not exclusively, relates to a technique to determine range of motion of a patient's cervical spine.

The use of prosthetic implants to address orthopedic injuries and ailments has become commonplace. With the development of a wide range of spinal prosthetic devices, there is a growing need for better ways to assess which device to use. For the cervical region, the ranges of motion in flexion, extension, left and right lateral bending, and axial rotation are often a consideration. Moreover, there is an ever present challenge to enable less invasive spinal surgery techniques, shorten the time required to surgically implant prosthetic devices, decrease patient recovery time, and/or provide other improvements. Thus, there is a need for additional contributions in this area of technology.

SUMMARY

One embodiment of the present application is a unique technique for assessing and medically treating the spine. Other embodiments include unique methods, systems, devices, kits, and apparatus involving the spine.

A further embodiment of the present application includes: determining a desired spinal lordosis model for a patient, shaping a support to conform to this lordosis, performing surgery based on the lordosis model provided by the support, and while holding the patient in the support to configure the patient's spine with the desired lordosis, moving the support to perform a range of motion assessment.

Still a further embodiment includes: determining a desired lordosis of a cervical spine of a patient, shaping a neck support to conform to the patient's neck positioned in accordance with this desired lordosis, implanting a prosthetic device in the cervical spine of the patient based on the desired lordosis, and moving the neck support to assess range of motion of the cervical spine with the prosthetic device implanted therein. In one form, the movement of the neck support includes pivoting about two different axes—one corresponding to a lateral bending range of motion for the neck and another corresponding to an axial rotation range of motion for the neck. Alternatively or additionally, such movement of the neck support may include pivoting about an axis that corresponds to range of motion in flexion and/or extension of the neck.

Another embodiment of the present application includes: shaping a neck support to conform to a neck of a patient positioned in accordance with a desired lordosis of a cervical spine of the patient, preparing the patient for implantation of a prosthetic device in the cervical spine during surgery by configuring the neck of the patient with the desired cervical lordosis through placement in the neck support, determining placement of the prosthetic device relative to the neck while the neck is configured with the desired lordosis in the neck support, and implanting the prosthetic device based on such placement.

Yet another embodiment includes: a neck support including a molded material to conform to a lordodic shape of a neck of a patient and to retain this shape. Also included is range of motion equipment and imaging equipment. The support is mounted to a member of the range of motion equipment, which is structured to pivot about a first axis and a second axis relative to an equipment base. The range of motion equipment is structured to receive the neck of the patient in the neck support while connected to the member to prepare for implantation of the prosthetic device in a cervical spine of the patient by configuring the neck of the patient with the lordodic shape.

One object of the present application is to provide a unique spinal evaluation technique.

Alternatively or additionally, another object of the present application is to provide a unique method, system, device, instrument, kit, and/or apparatus involving the spine.

Further embodiments, forms, features, aspects, benefits, objects, and advantages of the present application shall become apparent from the detailed description and figures provided herewith.

DETAILED DESCRIPTION OF SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations or further modifications of the described embodiments, and any further applications of the principles of the invention as described herein are contemplated as would normally occur to one skilled in the art to which the invention relates.

Figure 1:
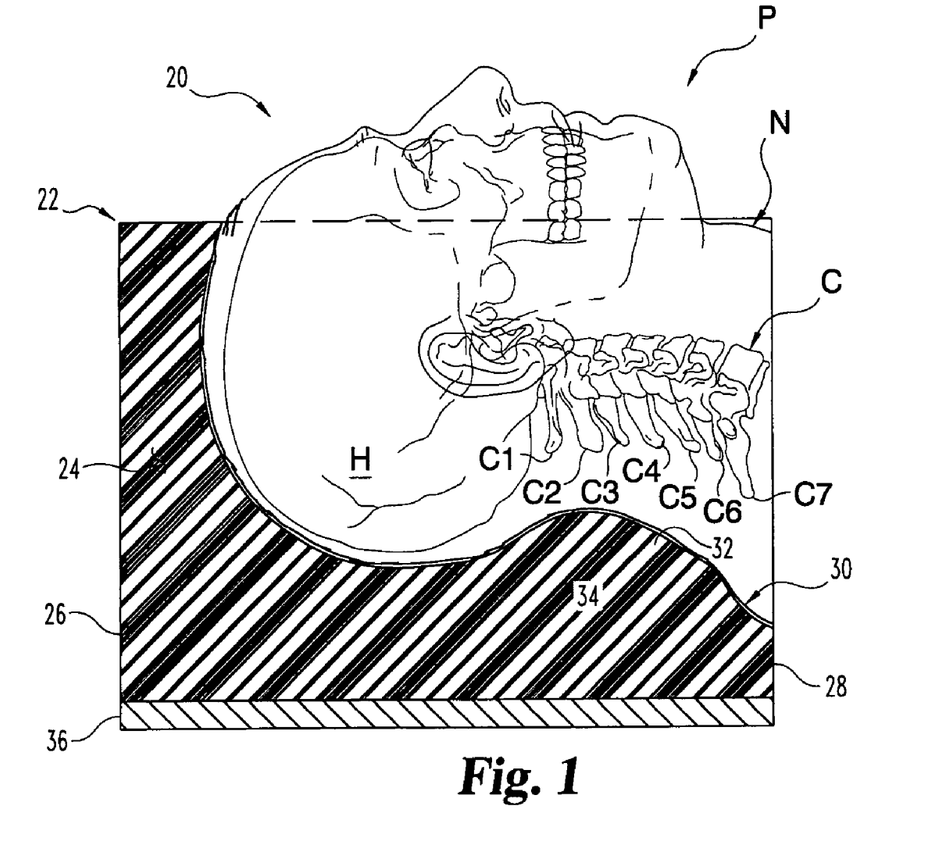
FIG. 1 is a partially diagrammatic, sectional side view of a neck support holding a patient.
Figure 3:
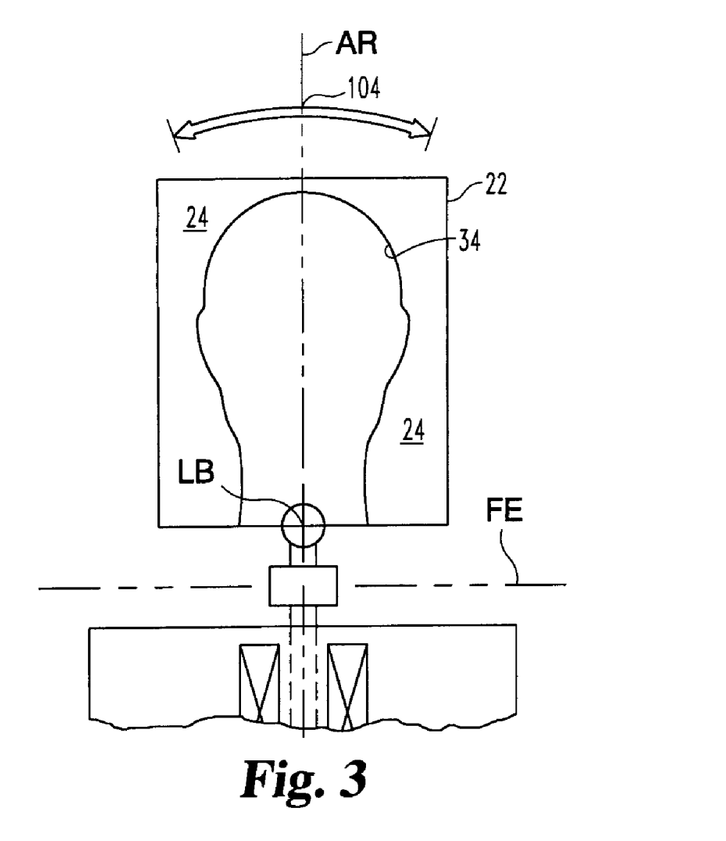
FIGS. 3 and 4 are partial views of the system of FIG. 2 with different view planes that correspond to view line 3-3 and sectional view line 4-4 shown in FIG. 2.
Figure 4:
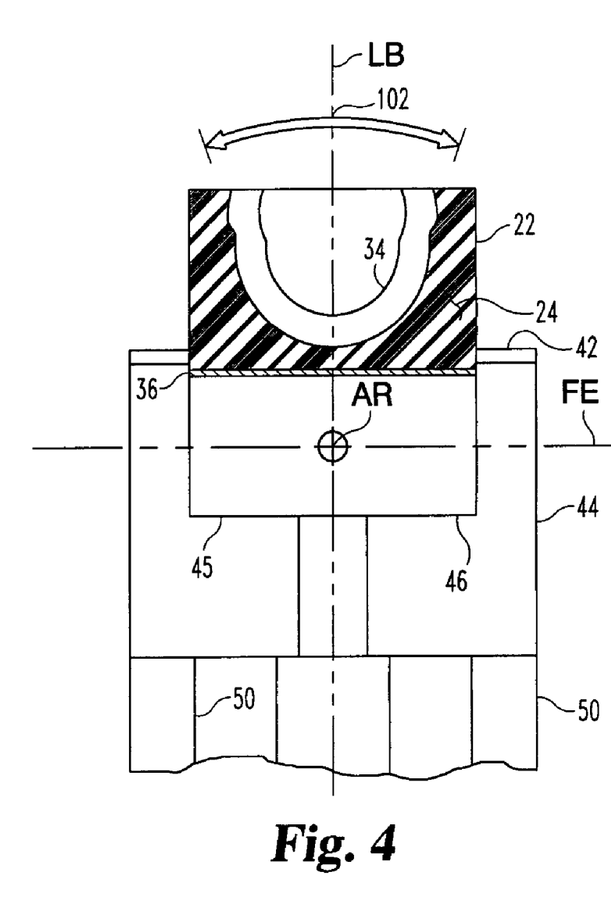

FIG. 1 depicts a portion of cervical evaluation system 20. System 20 includes neck support 22 holding patient P. Support 22 includes material 24 that is shaped to conform to at least an inferior portion of head H of patient P and neck N of patient P; where neck N corresponds to the seven cervical vertebrae C1-C7 or the patient's cervical spine C as shown in the partially diagrammatic, sectional side view of FIG. 1. Head H is more proximate to end portion 26 of support 22 and neck N is more proximate to end portion 28 of support 22. Correspondingly, contouring 30 results, including the lordodic profile 32 defined by sectioned material 24. It should be appreciated that contouring 30 provides a partial three-dimensional (3-D) impression 34 as further illustrated in the mutually perpendicular view planes of FIGS. 3 and 4. FIGS. 3 and 4 depict support 22 mounted to other equipment as will be more fully described hereinafter.

Material 24 is comprised of a manually moldable polymeric resin that readily conforms to head H and neck N and retains impression 34. In one form, material 24 initially can be shaped and reshaped manually or by the weight or force exerted by patient P, and once the desired shape is attained, it can be hardened to retain the desired shape (such as impression 34) through a curing, drying, or hardening process. Such processes can be performed in a standard manner based on the specific material type, such as bringing material 24 to a predefined curing temperature, exposing material 24 to ultraviolet (UV) light exposure, chemically treating material 24 with a fluid, or conformally coating material 24 with a substance that cures or dries to form a hard shell, just to name a few examples. Alternatively or additionally, material 24 can be formed to the desired impression by cutting, abrasion, ablation, or the like; or material 24 can be manually molded without curing or hardening—it being recognized that material 24 may then be more subject to unintended reshaping compared to other forms.

Support 22 includes base 36. Material 24 is connected to base 36. Support may further include one or more walls (not shown) that may extend from base 36 to contain and/or provide supporting margins for material 24.

Figure 2:
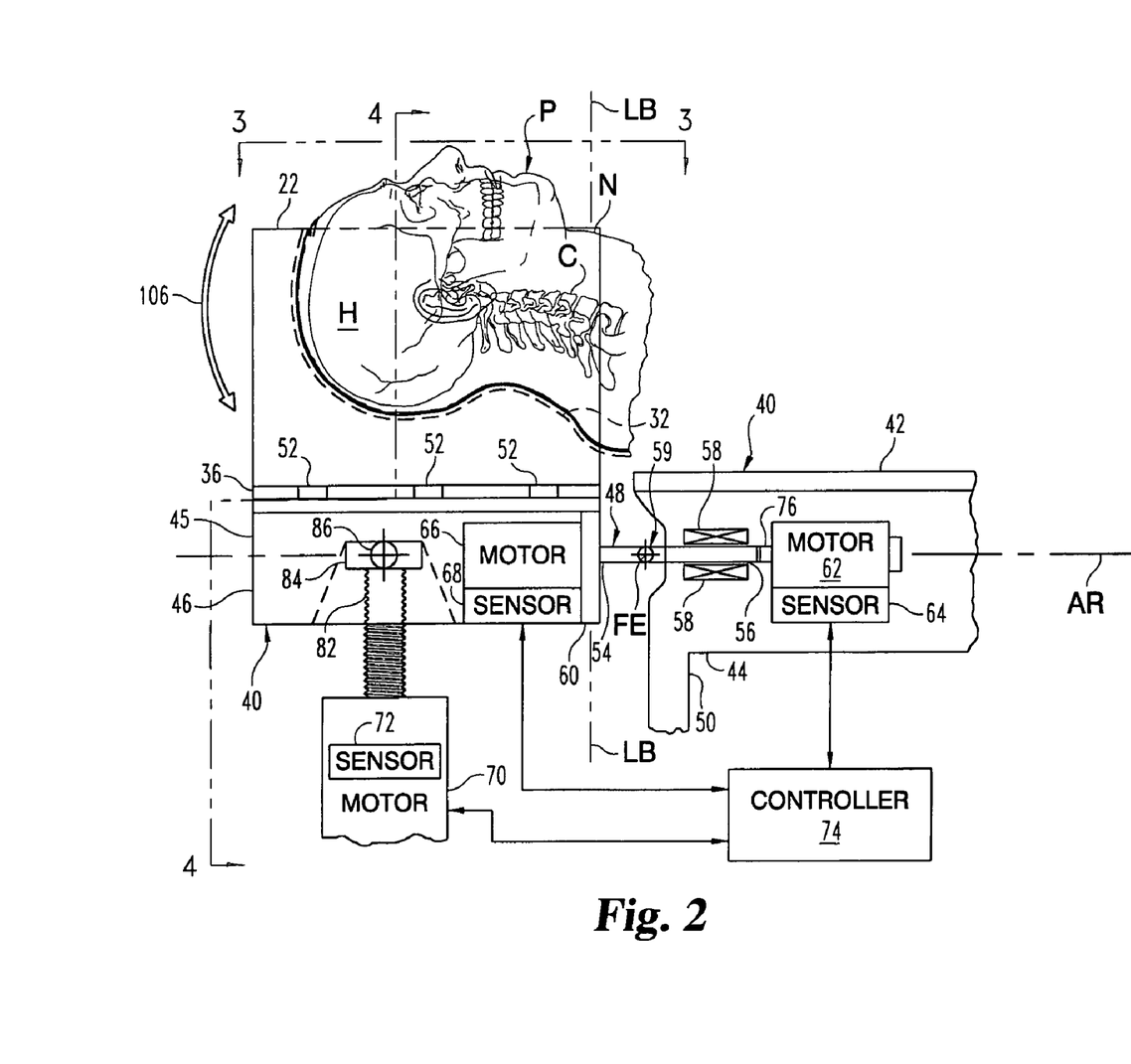
FIG. 2 is a partially diagrammatic view of a system including the neck support of FIG. 1 and range of motion equipment.

Referring additionally to FIG. 2, system 20 includes range of motion equipment 40 to which support 22 is mounted. Equipment 40 includes table 42 with base 44 and pivoting member 45 that is in the form of pivot table 46. Pivot table 46 is connected to base 44 by arm 48. Base 44 is arranged to engage the floor or ground through a plurality of legs, only one of which is illustrated as designated by reference numeral 50. Alternatively or additionally, base 44 can be supported by a pedestal (not shown), suspended from another structure, and/or be cantilevered to a wall (not shown), or the like.

Table 42 supports the portion of patient P's body inferior to that held in support 22 (not shown) and is structured to be generally fixed in relation to its surroundings while pivot table 46 selectively moves in relation to table 42 and its surroundings during use, as further described hereinafter. Support 22 is mounted and fixed to pivot table 46 by mounting structure 52 that includes a number of connectors detachably engaged to base 36.

Arm 48 includes pivoting end portion 54 opposite fixed end portion 56. Referring collectively to FIGS. 2-4, three mutually orthogonal view planes are represented; where view line 3-3 and sectional view line 4-4 in FIG. 2 correspond to FIGS. 3 and 4, respectively. The representation of patient P is omitted in FIGS. 3 and 4 to enhance clarity. End portion 54 is connected to table 46 in a fixed manner and end portion 56 is rotatably engaged to table 42 with schematically represented journal bearings 58 internal to base 44. This journaling of end portion 56 facilitates pivoting about rotation axis AR. Axis AR is represented by like-labeled crosshairs in FIG. 4. Pivot coupling 59 couples together end portion 54 and end portion 56 to facilitate pivoting about flexion-extension axis FE that is represented by like-labeled crosshairs in FIG. 2. Opposite coupling 59, end portion 54 is connected to pivot coupling 60 that facilitates pivoting about lateral axis LB. Axis LB is represented by like-labeled crosshairs in FIG. 3. Like the view planes of FIGS. 2-4, axes AR, FE, and LB are mutually orthogonal, and furthermore represent three degrees of rotational freedom of motion. Range of Motion (ROM) relative to each of these degrees of motion is commonly of interest in evaluating functional aspects of cervical spine C.

Equipment 40 also has several components schematically represented in FIG. 2, including: motor 62 and position sensor 64 included in base 44, motor 66 and position sensor 68 included in table 46, and motor 70 and sensor 72 located below table 46, all of which are operatively coupled to controller 74. Motor 62 includes rotatable shaft 76 that is connected to arm 48 to rotate about axis AR therewith. In response to certain control signals from controller 74, motor 62 selectively turns shaft 76 and, correspondingly turns arm 48 and table 46 about axis AR. Sensor 64 operates to provide position information signals to controller 74. Motor 66 is mechanically linked to coupling 60 to controllably cause rotation of table 46 about axis LB. Sensor 68 is arranged to report position information to controller 74.

Motor 78 is mechanically linked to plunger 80 by gearing, belts, rack and pinion, or the like. In response to certain control signals from controller 74, motor 78 operates to selectively move plunger 80 shaft up or down in a translation—following an approximately straight line path parallel to axis LB. End portion 82 of plunger 80 is rotatably coupled under table 46 by coupling 84. As plunger 80 moves up and down, table 46 pivots about axis FE, following an arcuate path. End portion 82 is pivotally coupled to table 46 by pin 86 of coupling 84 to reduce resistance that could arise because table 46 is moving in rotation as plunger 80 is moving in translation. Coupling 84 is also structured to facilitate pivoting of table 46 about axis AR without interference from the connection to plunger 80. Sensor 72 detects plunger position information and provides corresponding signals to controller 74.

Controller 74 can be of any type suitable to perform desired functions as predefined in corresponding controller operating logic of a software, firmware, and/or hardware variety. In one form, controller 74 is comprised of one or more electronic components that define digital circuitry, analog circuitry, or both. For this particular form, controller 74 may be one or more programmable digital or analog processors; a hardwired, dedicated state machine; or a combination of these. Controller 74 can include one or more types of memory, signal format converters or conditioners, power supplies, or the like desired for its implementation. Collectively, support 22 and equipment 40 provide one form of range of motion evaluation device 90, although many other forms are also contemplated and/or set forth herein as alternatives, variations, and/or options, to name a few. In particular, the evaluation of cervical range of motion with device 90 is further described in connection with FIG. 5 as follows.

Figure 5:
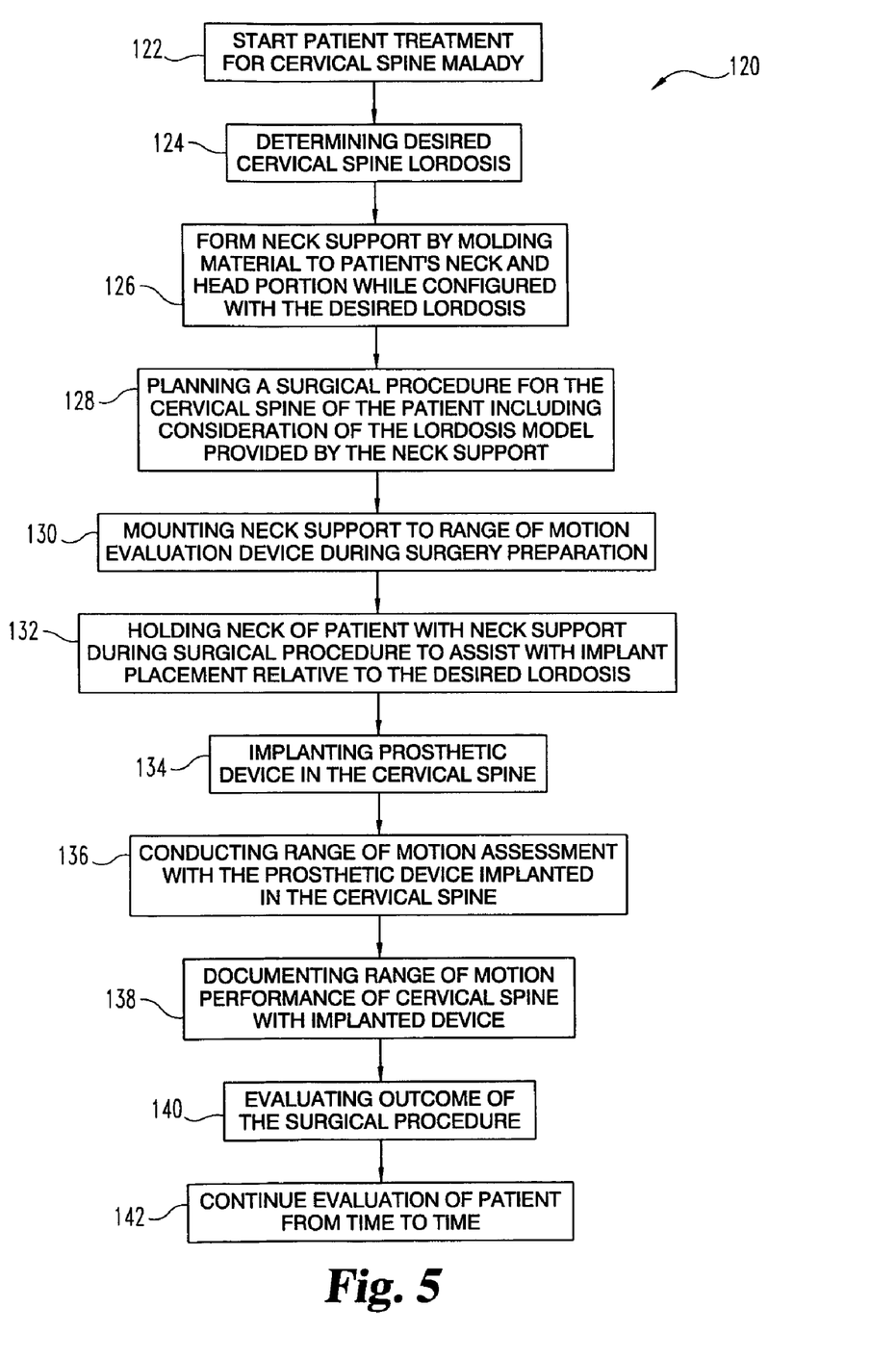
FIG. 5 is a flow chart of one procedure for using the system of FIG. 2.

FIG. 5 is a flowchart representing medical treatment 120 that includes the application of system 20. Treatment 120 is directed to a cervical spine malady of patient P, as might result from injury, disease, and/or congenital defect. Stage 122 represents an initial physician office visit by patient P near the beginning of treatment 120. The condition of cervical spine C is evaluated by the physician in stage 122. As part of this evaluation, the desired lordosis of cervical spine C is determined in stage 124. Typically, this determination is intended to be representative of patient P's normal or required posture while standing and performing Activities of Daily Living (ADL).

If surgery is indicated by this evaluation, treatment 120 proceeds from stage 124 to stage 126. In stage 126, material 24 of support 22 is shaped to conform to neck N of patient P while oriented with the desired lordosis determined in stage 124. This shaping is usually performed before support 22 is mounted to equipment 40. Such shaping can be of any type, including any of the varieties previously described in connection with support 22. As a result, a patient-specific lordosis model is captured as impression 34. At least in part, the surgeon plans the surgical procedure based on this model as represented in stage 128. Such planning frequently involves the selection of one or more prosthetic devices to implant in cervical spine C during surgery (a surgical "implantation" procedure), determining the particular surgical approach, and/or estimating the outcome.

After this pre-op planning in stage 128, the surgery is performed. Also, it should be appreciated that further physician office visits often occur before surgery that are not specifically depicted in the flowchart of FIG. 5. The surgical procedure includes a preparatory intra-op stage 130. In stage 130, the patient's neck N is placed in support 22 mounted to member 45 of equipment 40. Through this placement, neck N acquires the desired lordosis of cervical spine C. With this lordodic shape acquired, guess-work regarding the alignment and corresponding placement of one or more implants is typically reduced. Likewise, surgical instrumentation can often be more readily aligned and maintained in the proper position relative to neck N and cervical spine C.

From intro-op stage 130, treatment 120 continues with stage 134. In stage 134, surgery continues with implantation of the prosthetic device. It should be understood that equipment 40 provides a way to uniformly test and verify range of motion of cervical spine C about each of axes AR, LB, and FE. In FIGS. 2-4, these ranges are each represented by a double-headed arrow in a different one of FIGS. 2-4 and designated axial rotation range of motion 102, lateral bending range of motion 104, and flexion-extension range of motion 106, respectively. With the sensing and controller arrangement of equipment 40, the corresponding sensing information can be utilized to reproducibly quantify each range of motion and further determine speed of movement, among other things. Further, equipment 40 can be structured so that pivoting about only one of axes AR, LB, or FE is permitted at a time via selectable locking mechanisms or the like (not shown).

With these capabilities of equipment 40 in mind, stage 136 includes performing a motion assessment of cervical spine C during the surgical procedure to observe initial operation of the prosthetic device(s) implanted. This assessment can include measurement of axial rotation range of motion 102, lateral bending range of motion 104, and/or flexion-extension range of motion 106 using equipment 40 while neck N is held in support 22. From such measurement and/or other observations, the surgeon can selectively adjust or "fine tune" the prosthesis, as needed in stage 136. This assessment can also be preformed before surgery and/or before prosthetic device implantation to provide a comparison to the post-implantation assessment, or for other reasons.

Figure 6:
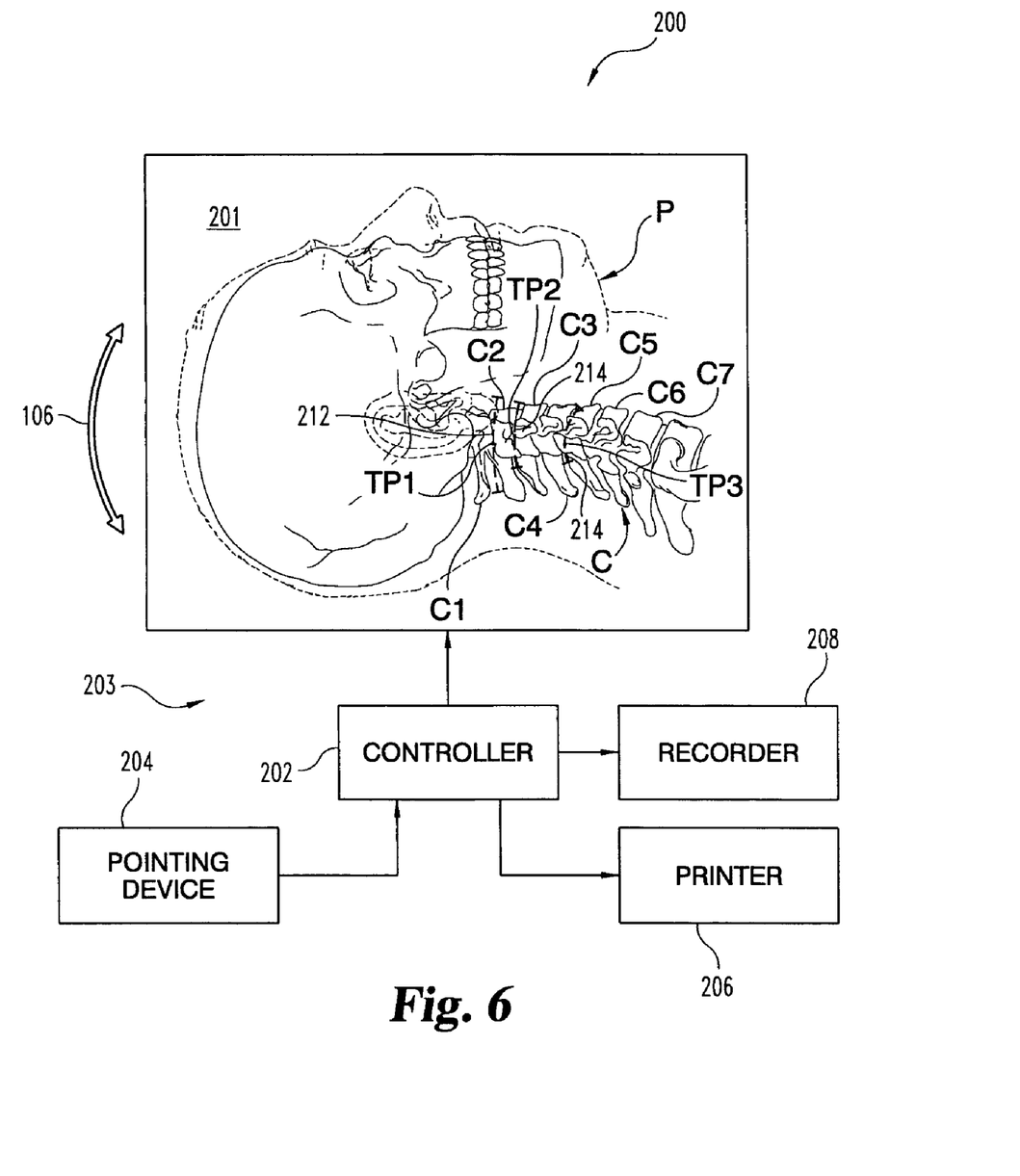
FIG. 6 is a partially diagrammatic view of an imaging device showing an image of a patient while using the system of FIG. 2 to evaluate range of motion of the patient's cervical spine.

During the range of motion assessment, imaging is performed to visualize cervical spine C. Such imaging can be fluoroscopic (x-ray based) or of another type suitable for use during the surgical procedure while patient P is held by support 22 mounted to table 46. FIG. 6 illustrates imaging equipment 200 that includes display 201. Equipment 200 also includes controller 202 and a number of Input/Output (I/O) devices 203, including display 201, pointing device 204, printer 206, and recorder 208. Controller 202 can be of any of the same hardware arrangements as described for controller 74 with operating logic adjusted to its different function. Pointing device 204 can be a mouse, light pen, digitizing pad, or the like. Printer 206 can be of any type suitable to generate images corresponding to display 201 of a desired resolution and chromaticity. Recorder 208 is configured to record multiframe/video and/or still images presented on display 201. Other types of I/O devices (not shown) can be additionally or alternatively included, such as a keyboard, loudspeaker, or the like.

Display 201 depicts internal imaging of patient P, while held by support 22, that is in turn mounted to equipment 40. Support 22 and equipment 40 are not depicted in FIG. 6 to enhance clarity. Equipment 200 is configured to generate still images and/or provide moving, multiframe imaging (video) of patient P during execution of stage 136 to document cervical performance. In one mode of operation, pointing device 204 can be utilized to mark a trace point on the image while table 46 is not moving relative to equipment 200. This trace point could be on any part of the image, but would typically be on one of the bones visualized during the imaging—such as one of the cervical vertebrae. Table 46 is then controllably articulated over a selected range of motion.

During this movement, the selected point traces a path as it travels that is typically arcuate and corresponds to the selected range of motion. FIG. 6 presents different traces 212, 214, and 216 each corresponding to different cervical vertebrae. Traces 212, 214, and 216 are indicative of flexion-extension range of motion 106 designated in FIG. 6 and as also represented along the view plane of FIG. 2. The initially selected three points TP1, TP2, and TP3 are also represented for traces 212, 214, and 216, respectively. It should be appreciated that equipment 200 includes the ability to provide imaging in the orthogonal view planes corresponding to FIGS. 3 and 4, too.

Accordingly, range of motion can be documented at both a global spine level and at selected lower levels, such as Focal Segment Units (FSU), specific vertebrae, or the like. In stage 138, the performance of the cervical spine with the implanted prosthetic device(s) is documented and the surgical implantation procedure it completed. In stage 140, post-operative outcome is evaluated relative to the pre-operative and/or intra-operative state. Stage 140 includes assessing post-operative range of motion of cervical spine C during and/or after patient P's recovery from surgery, and comparing the results of any pre-operative and/or intra-operative range of motion evaluations. Treatment 120 concludes with evaluation of patient P from time to time in stage 142.

There are many other alternative embodiments of the present application. In one example, the support includes a sensor array or other detection mechanism responsive to contact by the patient's neck N to electronically preserve a lordodic model of the cervical spine orientation. Alternatively or additionally, neck support shaping and model preservation can be performed with a malleable wire mesh, separately shaped and stacked layers to provide a laminated model form and/or is of a disposable type. In other examples, range of motion equipment to which the support is mounted is not powered or motorized, has different pivotable coupling(s) such as one or more ball joints, includes fewer sensors, lacks a controller, or operates with a single motor or other mechanical power source mechanically linked and structured to selectively power rotation about any of axes AR, LB, or FE. In yet other examples, such equipment includes fewer or different degrees of freedom of motion and corresponding ranges of motion, includes visual gauges/display(s) indicative of neck movement/position, is arranged to optionally measure force/pressure exerted by neck N during movement along a given motion range, includes feedback control of one or more of the motors based on sensed position information to limit or otherwise regulate movement, and/or includes a device to record position information.

In still another example, motors and sensors of the range of motion equipment are configured with an operational mode that assists with movement over one or more ranges of motion and another mode that provides an adjustable degree of resistance to such movement. A further example combines equipment 200 and equipment 40 in an integrated system that is regulated by a single controller. In still another example, equipment 40 is structured with a manual operating mode as an alternative or addition to sensors and/or motors. This example can be arranged so that all measurement and recording of position information, range of motion, and the like is provided by imaging apparatus.

In another embodiment, a neck support is provided with a polymeric material having a manually moldable state and structured to conform to a desired lordodic shape of a patient's neck. This support can include a base mountable to other equipment, such as equipment 40, and/or can be of a disposable type. In one particular form, the neck support is sterilizable.

Still a further embodiment includes: means for supporting a neck of a patient while positioned in a desired lordodic shape. The supporting means includes a polymer material with a moldable state. Also included is means for selectively pivoting the supporting means about each of at least two mutually perpendicular axes, and means for imaging a patient's cervical spine held in the support as it pivots.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:
   determining a desired lordosis of a cervical spine of a patient;
   shaping a neck support to conform to a neck of the patient positioned in accordance with the desired lordosis;
   implanting a prosthetic device in the cervical spine of the patient based on the desired lordosis; and
   while holding the neck of the patient in the neck support to configure the neck with the desired cervical lordosis, moving the neck support to assess range of motion of the cervical spine with the prosthetic device received therein.

2. The method of claim 1, wherein said shaping includes molding a polymer material to the neck shape and at least a portion of a head of the patient.

3. The method of claim 1, which includes documenting the range of motion by imaging the cervical spine during said moving.

4. The method of claim 1, wherein said moving includes:
   pivoting the neck support about a first axis to determine a lateral bending range of motion of the neck; and
   pivoting the neck support about a second axis to determine an axial rotation range of motion of the neck.

5. The method of claim 4, which includes:
   providing equipment including a base pivotally connected to a pivoting member; and
   coupling the neck support to the pivoting member, the pivoting member being structured to controllably pivot the neck support about the first axis and the second axis, and being further structured to pivot the neck support about a third axis to determine at least one of a flexion and extension range of motion of the neck.

6. The method of claim 1, wherein said moving is performed before a surgical procedure to implant the prosthetic device is completed.

7. The method of claim 1, wherein said moving is performed post-operatively to evaluate outcome of surgery to implant the prosthetic device.

8. The method of claim 1, which includes assessing placement of the prosthetic device while holding the neck of the patient in the neck support to prepare for said implanting.

9. A method, comprising:
   providing a neck support shaped to conform to a neck of a patient with a desired lordosis of a cervical spine of the patient;
   performing a surgical procedure on the cervical spine of the patient based on the desired lordosis;
   during or after the surgical procedure, holding the neck of the patient in the neck support to configure the neck with the desired cervical lordosis and pivoting the neck support about two or more different pivot axes during said holding to evaluate two or more different ranges of motion of the cervical spine of the patient.

10. The method of claim 9, wherein the two or more ranges of motion include an axial rotation range of motion corresponding to said pivoting about one of the axes and a lateral bending range of motion corresponding to said pivoting about another of the axes.

11. The method of claim 10, wherein the two or more ranges of motion include at least one of a flexion or extension range of motion of the neck correspond to said pivoting about a further one of the axes.

12. The method of claim 9, which includes molding a polymer material to retain the desired lordosis with the neck support.

13. The method of claim 9, wherein said pivoting is performed before implanting a prosthetic device in the cervical spine during the procedure.

14. The method of claim 9, wherein said pivoting is performed after completion of the surgical procedure to evaluate surgical outcome.

15. The method of claim 14, which includes generating an image of the cervical spine during performance of said pivoting.

16. A method, comprising:
   providing a neck support shaped to conform to a neck of a patient positioned in accordance with a desired lordosis of a cervical spine of the patient;
   to prepare the patient for implantation of a prosthetic device in the cervical spine during surgery, configuring the neck of the patient with the desired cervical lordosis by placing the neck in the neck support;
   while the neck is configured with the desired cervical lordosis in the neck support, determining placement of the prosthetic device relative to the neck and cervical spine; and
   implanting the prosthetic device based on the placement.

17. The method of claim 16, wherein said providing includes molding a polymer material to the neck and at least a portion of a head of the patient.

18. The method of claim 16, wherein said determining includes moving the neck support over one or more ranges of motion of the neck.

19. The method of claim 16, which includes:
   providing an evaluation device including a base pivotally connected to an articulating member; and
   coupling the neck support to the articulating member, the articulating member being structured to controllably pivot the neck support about one or more axes to evaluate one or more corresponding ranges of motion of the neck.

20. The method of claim 16, which includes:
pivoting the neck support about one axis corresponding to a cervical lateral bending range of motion and about another axis corresponding to a cervical axial rotation range of motion; and
generating an image of the cervical spine during performance of said pivoting.

21. Apparatus, comprising:
a neck support including a moldable material to conform to a lordodic shape of a neck of a patient and retain the lordodic shape;
range of motion equipment including a base and an pivoting member, the pivoting member including mounting structure to detachably connect to the neck support, the pivoting member being connected to the base by one or more couplings to pivot about a first pivot axis and a second pivot axis, the range of motion equipment being structured to receive the neck of the patient in the neck support while connected to the pivoting member to prepare for implantation of a prosthetic device in a cervical spine of the patient by configuring the neck of the patient with the lordodic shape; and
imaging equipment structured to visualize the cervical spine of the patient when positioned in a desired location relative to the equipment holding the patient's neck in the neck support, the imaging equipment being structured to document range of motion of the cervical spine during pivoting with the range of motion equipment.

22. The apparatus of claim 21, wherein the first axis is approximately orthogonal to the second axis, the range of motion equipment is structured to pivot about a third axis, and the third axis is approximately orthogonal to the first axis and the second axis.

23. The apparatus of claim 21, further comprising means for forming a trace on one or more images provided with the imaging equipment.

24. The apparatus of claim 21, wherein the range of motion equipment includes one or more motors.

25. The apparatus of claim 21, wherein the imaging equipment includes an x-ray source.

* * * * *